(12) United States Patent
Shen

(10) Patent No.: US 9,147,244 B2
(45) Date of Patent: Sep. 29, 2015

(54) METHOD OF ULTRASOUND NONLINEAR IMAGING WITH HIGH-BIT GOLAY CODE EXCITATION

(71) Applicant: NATIONAL TAIWAN UNIVERSITY, Taipei (TW)

(72) Inventor: Che-Chou Shen, Taipei (TW)

(73) Assignee: National Taiwan University, Taipei (TW)

( * ) Notice: Subject to any disclaimer, the term of this patent is extended or adjusted under 35 U.S.C. 154(b) by 72 days.

(21) Appl. No.: 14/197,332

(22) Filed: Mar. 5, 2014

(65) Prior Publication Data

US 2015/0117734 A1 Apr. 30, 2015

(30) Foreign Application Priority Data

Oct. 28, 2013 (TW) .............................. 102138887 U

(51) Int. Cl.
*G06K 9/00* (2006.01)
*G06T 7/00* (2006.01)
(52) U.S. Cl.
CPC .................................. *G06T 7/0012* (2013.01)
(58) Field of Classification Search
None
See application file for complete search history.

(56) References Cited

U.S. PATENT DOCUMENTS

| 6,050,947 A * | 4/2000 | Rhyne et al. ................... 600/447 |
| 2002/0049381 A1* | 4/2002 | Eck et al. ...................... 600/447 |

OTHER PUBLICATIONS

Qin et al (NPL: "Contrast enhanced of medical ultrasound imaging with reversal phase-inversion pulse technology", J. Cent. South Univ. (2013) 20: 696 701).*
Shen et al (NPL: Slow-time Golay Decoding for Doppler Detection of High-velocity Blood Flow, 10.1109/ULTSYM (2013) 0377, IEEE).*

* cited by examiner

*Primary Examiner* — Bhavesh Mehta
*Assistant Examiner* — Oneal R Mistry
(74) *Attorney, Agent, or Firm* — Rosenberg, Klein & Lee

(57) ABSTRACT

A method of ultrasound nonlinear imaging with high-bit Golay code excitation includes transmitting a first, a second, a third and a fourth Golay code signal wave which have more than four bits and are orthogonal pairs to each other; making the second and the forth Golay code signal wave be subtracted from the first and the third Golay code signal wave respectively to eliminate noise interference wave; performing compression filtering process to the above generated waves and taking a cross sum to generate two compressed code waves; taking the difference between the two compressed code waves to generate an image wave which includes at least two second-order harmonic waves; processing ultrasound nonlinear imaging by using the second-order harmonic waves and to generate an ultrasound image.

5 Claims, 6 Drawing Sheets

METHOD OF ULTRASOUND NONLINEAR IMAGING WITH HIGH-BIT GOLAY CODE EXCITATION

FIELD OF THE INVENTION

The present invention is related to a method of ultrasound nonlinear imaging with high-bit Golay code excitation, and more particularly to a method using orthogonal high-bit Golay code to eliminate noise interference of neighboring frequency band to enhance resolution and using the multi-frequency components of the wave to proceed ultrasound nonlinear imaging.

BACKGROUND OF THE INVENTION

Traditional ultrasound imaging method adopts linear scattered fundamental signal to image. However, the fundamental signal is susceptible to phase aberration due to the presence of fat layer in the shallow tissue or skin and will result in low imaging quality. As the sound wave is traveling in human tissues during the imaging process, the wave signal will have finite amplitude distortion or generate harmonic signals when encountering strong nonlinear medium such as microbubble contrast agents. When processing tissue imaging, because the magnitude of harmonic signals is lower than the fundamental signal in the beginning, the scattered harmonic signal will suffer from less phase aberration when penetrating the shallow tissue. Thus, tissue harmonic imaging can provide better contrast resolution because it is less susceptible to phase aberration and thus is broadly used in clinical diagnosis.

The contrast agents being used for harmonic imaging are composed of microbubbles. These small bubbles will have harmonic oscillation to generate lots of strong harmonic signals back to the probe when being excited by sound waves. Clinically, the contrast agents are injected into the blood vessel such that the blood vessel would be filled with micro bubbles to strengthen harmonic signals so as to generate a clearer image of blood vessel structure and blood perfusion. That is, the image contrast is enhanced.

A major difference between ultrasound fundamental signal and harmonic signal is the frequency range of echo signal. If the central frequency of the ultrasound signal travelling into the human body is $f_0$, the imaging method using the frequency signal $f_0$ of the echo signal is called fundamental imaging, but the imaging method using the harmonic signals with higher frequency, such as $2f_0$, $3f_0$, is called harmonic imaging. Because these harmonic signals are originated from the nonlinear reaction of the medium to the emitted ultrasound signal, harmonic imaging can be also regarded as nonlinear imaging. As mentioned, it is understood that by using a low frequency filter or high frequency filter to select the frequency range to be received, it is capable to decide whether fundamental imaging or harmonic imaging is performed. The discussion focuses on the analysis of components of second harmonic signal because the second harmonic signal is the strongest one among the various harmonic signals.

Although harmonic imaging is of great importance in clinical diagnosis due to better imaging quality, its weak signal intensity is a major drawback and may significantly degrade imaging sensitivity and penetration. Generally speaking, harmonic signal can be at least 20 db weaker than the fundamental signal even at the focus. Thus, there have been some researches and inventions focusing on using code excitation to enhance harmonic wave intensity. Among the various coding technologies, Golay code is easy to use and is quite applicable to code excitation. Golay code is performed by phase coded sequence. That is, the emitted signal has the phase 0° is represented by the symbol [1], the emitted signal has the phase 90° is represented by the symbol [j], the emitted signal has the phase 180° is represented by the symbol [−1], and the emitted signal has the phase 270° is represented by the symbol [−j]. Golay code featuring phase coding can be easily implemented on the hardware. However, Golay code excitation needs two emitting processes A and B to generate the corresponding echo signals complementary to each other. That is, the autocorrelation results of the two echo signals can be summed to totally remove the sidelobe interference.

Multi-frequency excitation has been developed in ultrasound nonlinear imaging. The feature of multi-frequency excitation is to emit multiple frequency components rather than single frequency component. If only considering the second-order nonlinear components, the ultrasound nonlinear signals generated by multi-frequency excitation will include the second harmonic signals of each emitting frequencies and the inter-modulation signal between the emitting frequencies. Thus, in addition to the second harmonic signals being used in typical harmonic imaging, the inter-modulation signals can also be used for generating image. However, multi-frequency excitation using Golay code excitation for imaging will result in incorrect coding of some harmonic wave components, such as second-order harmonic wave and fourth-order harmonic wave. These incorrectly coded components will interfere with the correctly coded signals to cause degradation in imaging quality.

Take nonlinear imaging using two-bit dual-frequency Golay excitation as an example, it is capable to have the frequency components $f_2-f_1$ and $2f_1$ of the second-order harmonic wave showing the correct code [1, −1] during emission A and the correct code [−1, −1] during emission B as shown in the following table. The above mentioned frequency components of the second-order harmonic wave are usually within the pass band of the probe and thus serve as the major signal components for imaging.

|  | Transmit | | $2^{nd}$-order Harmonic | | | 4th order Harmonic | | |
|---|---|---|---|---|---|---|---|---|
| Frequency | $f_1$ | $f_2$ | $f_2 - f_1$ | $2f_1$ | $f_2 + f_1$ | $f_2 - f_1$ | $2f_1$ | $f_2 + f_1$ |
| Golay code (Emission A) | [1, j] | [1, −j] | [1, −1] | [1, −1] | [1, 1] | [1, 1] | [1, −1] | [1, −1] | [1, 1] | [1, 1] |
| Golay code (Emission B) | [j, j] | [−j, −j] | [−1, −1] | [−1, −1] | [1, 1] | [1, 1] | [−1, −1] | [−1, −1] | [1, 1] | [1, 1] |

However, as shown in this table, it is understood that among the other harmonic wave components, component $f_2+f_1$ of the second-order harmonic wave and components $f_2-f_1$ and $2f_1$ of the fourth-order harmonic wave may not accord with the designed Golay code. The codes are all [1, 1]. These frequency components with incorrect code will result in unremovable sidelobe signals during the compression process and the method nowadays cannot effectively resolve this problem.

BRIEF SUMMARY OF INVENTION

As mentioned, when using high-bit Golay code excitation in multi-frequency harmonic imaging, it is demanded to: (1) enhance signal-to-noise ratio (SNR); (2) prevent the correctly coded signals from being interfered by the incorrectly coded components. However, the method provided in the publications nowadays can only achieve the first request but fail to disclose a concrete method to achieve both the two above mentioned requests when using high-bit Golay code excitation in multi-frequency harmonic imaging.

Accordingly, it is a main object of the present invention to provide a method of ultrasound nonlinear imaging with high-bit Golay code excitation. The method emits four sets of high-bit Golay code which are orthogonal with each other, removes the noise interference in the four sets of Golay code, and compresses the signals to generate the multi-frequency harmonic waves for imaging.

Based on the above mentioned object, a method of ultrasound nonlinear imaging with high-bit Golay code excitation is provided in accordance with an embodiment of the present invention. The method comprises the steps of:

(a) receiving a first Golay code signal wave, a second Golay code signal wave, a third Golay signal wave, and a fourth Golay signal wave, wherein the first Golay code signal wave includes at least two first second-order harmonic waves and at least one first noise interference wave, the second Golay code signal wave includes at least two second second-order harmonic waves and at least one second noise interference wave, the third Golay code signal wave includes at least two third second-order harmonic waves and at least one third noise interference wave, the fourth Golay code signal wave includes at least two fourth second-order harmonic waves and at least one fourth noise interference wave, the above mentioned at least two first second-order harmonic waves are respective to a first code signal and a second code signal, the above mentioned at least two second second-order harmonic waves are respective to the exchanged second code signal and the first code signal, the above mentioned at least two third second-order harmonic waves are respective to a third code signal and a fourth code signal, the above mentioned at least two fourth second-order harmonic waves are respective to the exchanged fourth code signal and the third code signal, the first code signal and the third code signal compose a first complementary pair, the second code signal and the fourth code signal compose a second complementary pair, and the first complementary pair and the second complementary pair are orthogonal by each other; and (b) making the second Golay code signal wave be subtracted from the first Golay code signal wave to eliminate the first noise interference wave and the second noise interference wave to generate a fifth Golay code signal wave, and making the fourth Golay code signal wave be subtracted from the third Golay code signal wave to eliminate the third noise interference wave and the fourth noise interference wave to generate a sixth Golay code signal wave.

In addition, after completion of step (b), further comprises: (c) performing a first compression filtering process and a second compression filtering process to the fifth Golay code signal wave respectively to generate a first compressed code signal wave and a second compressed code signal wave, and performing a third compression filtering process and a fourth compression filtering process to the sixth Golay code signal wave respectively to generate a third compressed code signal wave and a fourth compressed code signal wave; (d) taking a sum of the first compressed code signal wave and the third compressed code signal wave to generate a fifth compressed code signal wave, which includes at least two first compressed second-order harmonic waves, and taking a sum of the second compressed code signal wave and the fourth compressed code signal wave to generate a sixth compressed code signal wave, which includes at least two second compressed second-order harmonic waves; (e) taking the difference between the fifth compressed code signal wave and the sixth compressed code signal wave to generate an image wave which includes at least two imaging second-order harmonic waves; and (f) processing ultrasound nonlinear imaging by using the at least two imaging second-order harmonic waves to generate an ultrasound image; wherein, the first code signal, the second code signal, the third code signal, and the fourth code signal are high-bit code signals with more than four bits.

In accordance with a preferred embodiment of the method of ultrasound nonlinear imaging with high-bit Golay code excitation of the present invention, code signal of the first noise interference wave is generated by taking dot product of the first code signal with the second code signal, code signal of the second noise interference wave is generated by taking dot product of the second code signal with the first code signal, code signal of the third noise interference wave is generated by taking dot product of the third code signal with the fourth code signal, code signal of the fourth noise interference wave is generated by taking dot product of the fourth code signal with the third code signal. In addition, in accordance with a preferred embodiment of the present invention, in the step (b), the fifth Golay code signal includes at least two fifth second-order harmonic waves, and the at least two fifth second-order harmonic waves are generated by subtracting the at least two second second-order harmonic waves from the at least two first second-order harmonic waves.

Moreover, in accordance with a preferred embodiment of the present invention, in the step (b), the sixth Golay code signal includes at least two sixth second-order harmonic waves, and the at least two sixth second-order harmonic waves are generated by subtracting the at least two fourth second-order harmonic waves from the at least two third second-order harmonic waves. In addition, in accordance with a preferred embodiment of the present invention, in the step (c), the first compression filtering process is performed by cross-correlation of the fifth Golay code signal wave and the first code signal, the second compression filtering process is performed by cross-correlation of the fifth Golay code signal wave and the second code signal, the third compression filtering process is performed by cross-correlation of the sixth Golay code signal wave and the third code signal, and the fourth compression filtering process is performed by cross-correlation of the sixth Golay code signal wave and the fourth code signal.

The method of ultrasound nonlinear imaging with high-bit Golay code excitation in accordance with the present invention removes the interference signals prior to the compression process such that the high-bit Golay code can be correctly decoded. Thus, by using the Golay code waveform provided in the present invention, not only the SNR can be enhanced but also the problem of interference from the incorrectly coded components can be resolved so as to enhance imaging quality.

The embodiments adopted in the present invention would be further discussed by using the following paragraph and the figures for a better understanding.

DETAILED DESCRIPTION OF THE INVENTION

There are various embodiments of the method of ultrasound nonlinear imaging with high-bit Golay code excitation in accordance with the present invention, which are not repeated hereby. The preferred embodiments are mentioned in the following paragraph as an example. It should be understood by those skilled in the art that the preferred embodiments disclosed in the following paragraph are merely an example instead of restricting the scope of the invention itself.

Figure 1:
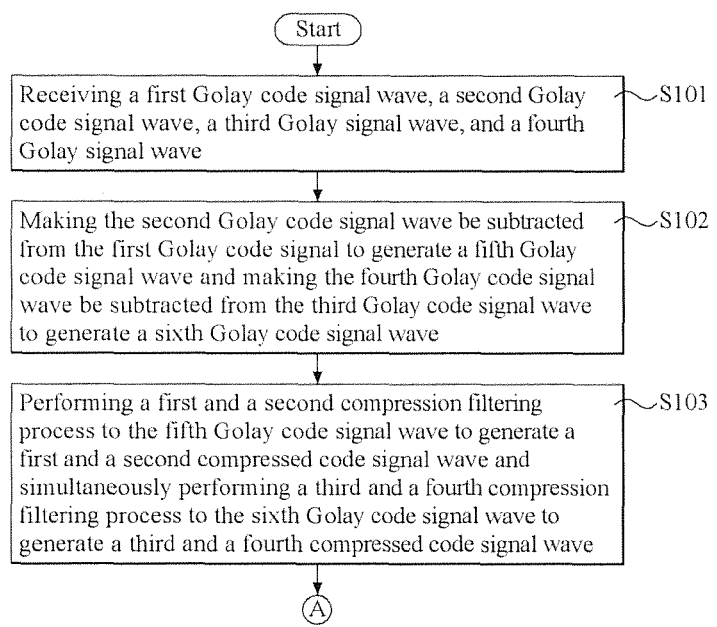
FIG. 1 and FIG. 1A are flow charts showing a method of ultrasound nonlinear imaging with high-bit Golay code excitation in accordance with a preferred embodiment of the present invention.
Figure 1A:
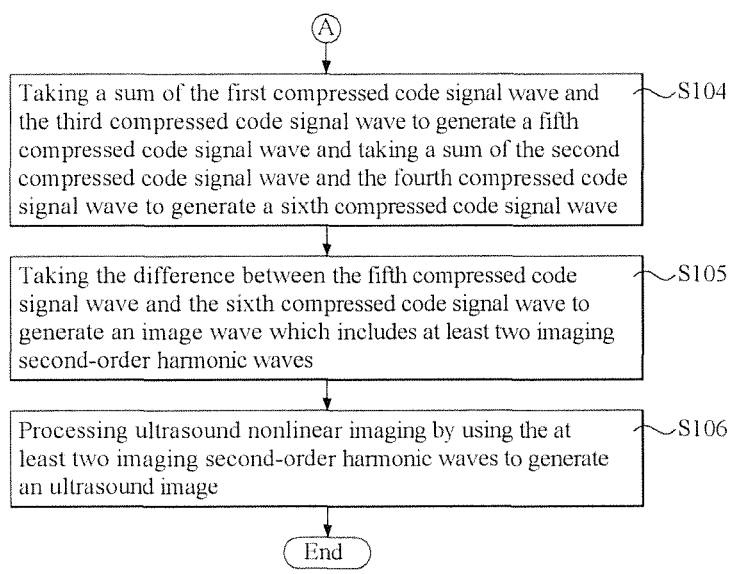
Figure 2:
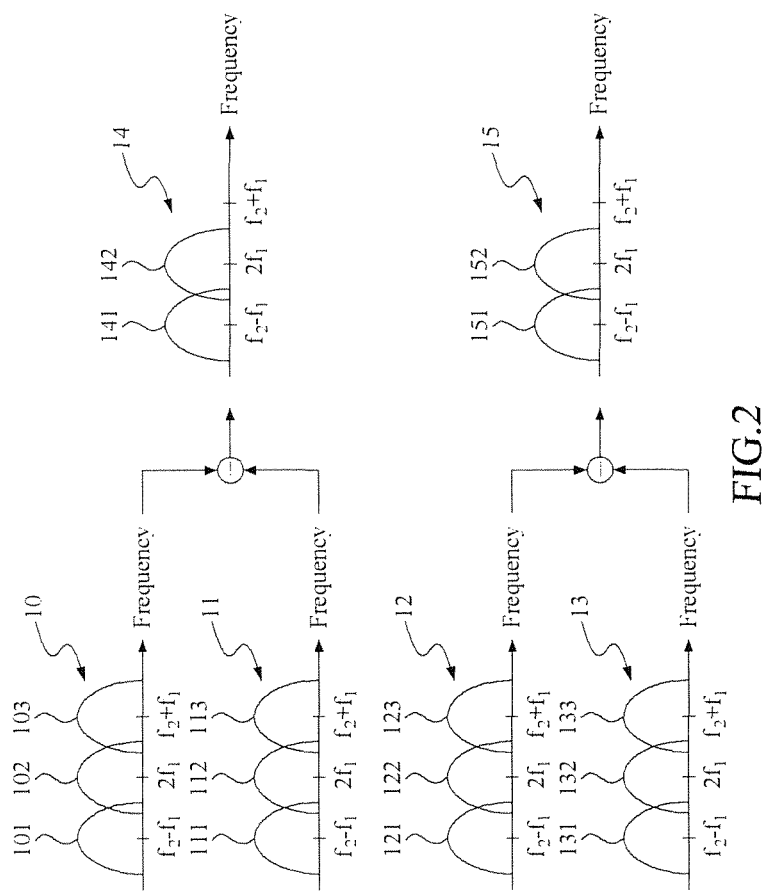
FIG. 2 is a schematic view showing the first Golay code signal wave, the second Golay code signal wave, the third Golay code signal wave, the fourth Golay code signal wave, the fifth Golay code signal wave, and the sixth Golay code signal wave in accordance with a preferred embodiment of the present invention.
Figure 3:
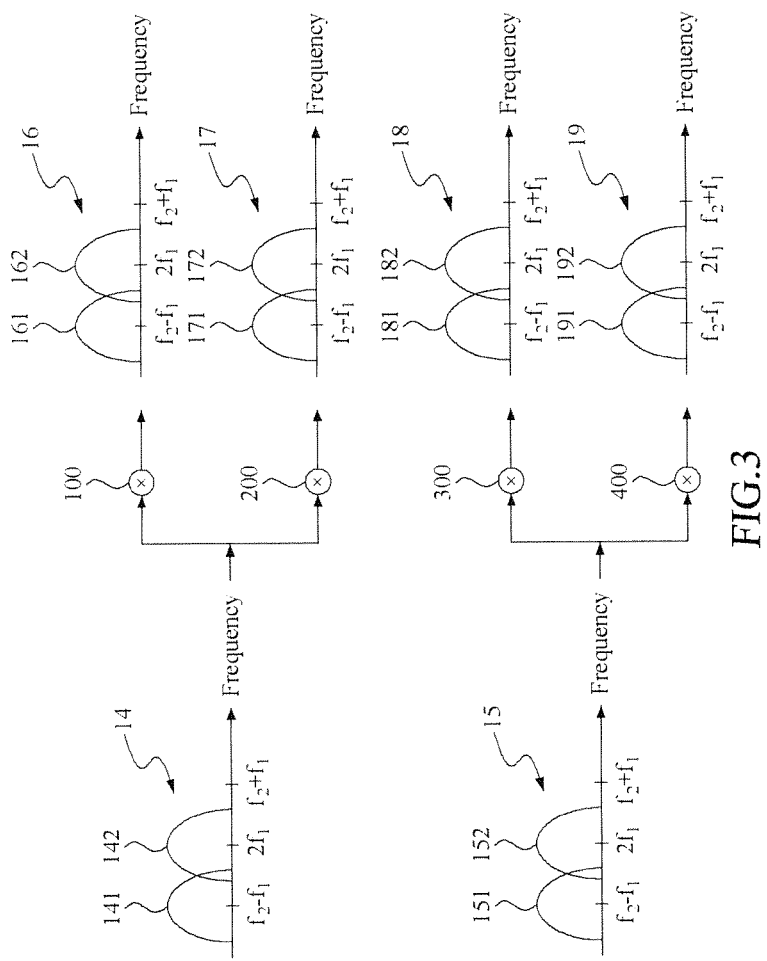
FIG. 3 is a schematic view showing the generation of the first compressed code signal wave, the second compressed code signal wave, the third compressed code signal wave, and the fourth compressed coded signal wave in accordance with a preferred embodiment of the present invention.
Figure 4:
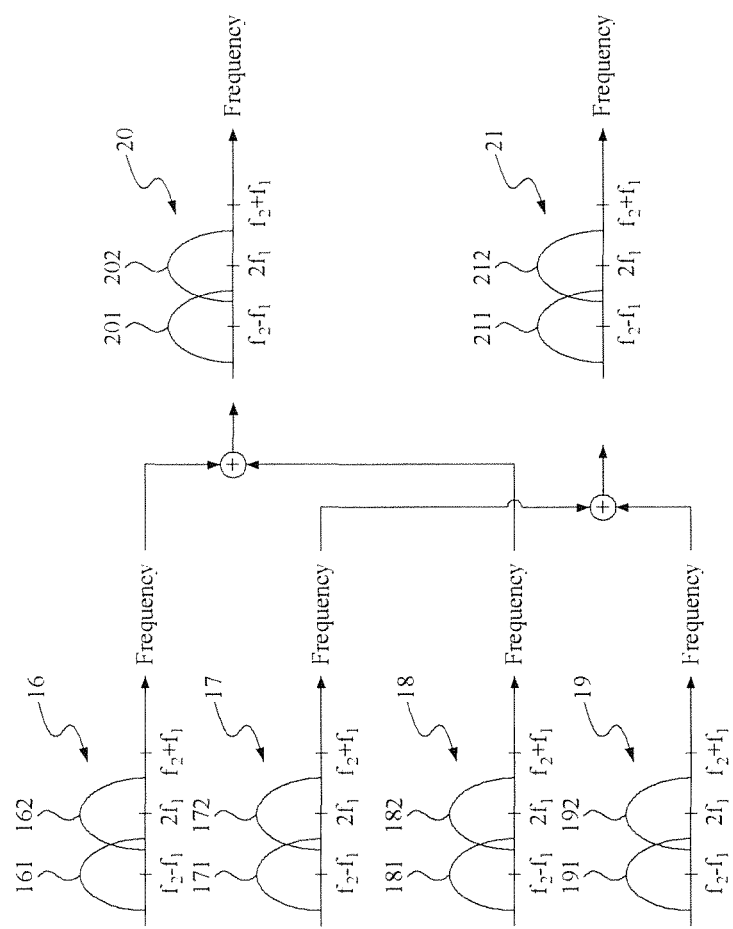
FIG. 4 is a schematic view showing the generation of fifth compressed code signal wave and the sixth compressed code signal wave in accordance with a preferred embodiment of the present invention.
Figure 5:
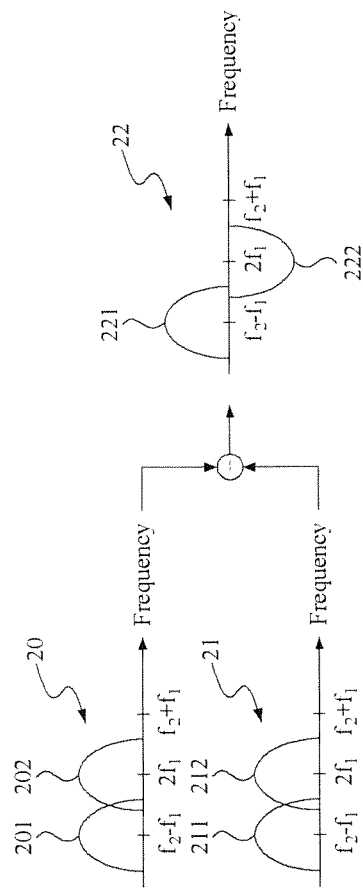
FIG. 5 is a schematic view showing the generation of the image wave in accordance with a preferred embodiment of the present invention.

Please refer to FIG. 1 to FIG. 5, wherein FIG. 1 and FIG. 1A are flow charts showing a method of ultrasound nonlinear imaging with high-bit Golay code excitation in accordance with a preferred embodiment of the present invention, FIG. 2 is a schematic view showing the first Golay code signal wave, the second Golay code signal wave, the third Golay code signal wave, the fourth Golay code signal wave, the fifth Golay code signal wave, and the sixth Golay code signal wave in accordance with a preferred embodiment of the present invention, FIG. 3 is a schematic view showing the generation of the first compressed code signal wave, the second compressed code signal wave, the third compressed code signal wave, and the fourth compressed coded signal wave in accordance with a preferred embodiment of the present invention, FIG. 4 is a schematic view showing the generation of fifth compressed code signal wave and the sixth compressed code signal wave in accordance with a preferred embodiment of the present invention, and FIG. 5 is a schematic view showing the generation of the image wave in accordance with a preferred embodiment of the present invention.

As shown, the method of ultrasound nonlinear imaging with high-bit Golay code excitation provided in accordance with a preferred embodiment of the present invention comprises the steps of:

Step S101: receiving a first Golay code signal wave, a second Golay code signal wave, a third Golay signal wave, and a fourth Golay signal wave;

Step S102: making the second Golay code signal wave be subtracted from the first Golay code signal to generate a fifth Golay code signal wave and making the fourth Golay code signal wave be subtracted from the third Golay code signal wave to generate a sixth Golay code signal wave;

Step S103: performing a first and a second compression filtering process to the fifth Golay code signal wave to generate a first and a second compressed code signal wave and simultaneously performing a third and a fourth compression filtering process to the sixth Golay code signal wave to generate a third and a fourth compressed code signal wave;

Step S104: taking a sum of the first compressed code signal wave and the third compressed code signal wave to generate a fifth compressed code signal wave and taking a sum of the second compressed code signal wave and the fourth compressed code signal wave to generate a sixth compressed code signal wave;

Step S105: taking the difference between the fifth compressed code signal wave and the sixth compressed code signal wave to generate an image wave which includes at least two imaging second-order harmonic waves; and Step S106: processing ultrasound nonlinear imaging by using the at least two imaging second-order harmonic waves to generate an ultrasound image.

After the process starts, step S101 is carried out to receive a first Golay code signal wave, a second Golay code signal wave, a third Golay code signal wave, and a fourth Golay code signal wave. As shown in FIG. 2, four phase coding waves with frequency $f_1$ and $f_2$ ($f_2$ is greater than $f_1$) are emitted before the present step, the first Golay code signal wave 10, the second Golay code signal wave 11, the third Golay code signal wave 12, and the fourth Golay code signal wave 13 are received by adjusting the phase. The first Golay code signal wave 10 includes two first second-order harmonic waves 101, 102 (in the other embodiments, the Golay code signal wave may include more than two second-order harmonic waves) and a first noise interference wave 103 (in the other embodiments, the Golay code signal wave may include more than one noise interference wave).

The second Golay code signal wave 11 includes two second second-order harmonic waves 111, 112 (in the other embodiments, the Golay code signal wave may include more than two second-order harmonic waves) and a second noise interference wave 113 (in the other embodiments, the Golay code signal wave may include more than one noise interference wave). The Third Golay code signal wave 12 includes two third second-order harmonic waves 121, 122 (in the other embodiments, the Golay code signal wave may include more than two second-order harmonic waves) and a third noise interference wave 123 (in the other embodiments, the Golay code signal wave may include more than one noise interference wave).

Specifically, the first second-order harmonic wave 101 and the second second-order harmonic wave 112 are with respective to a first code signal (not shown). As a preferred embodiment of the present invention, the code of the first code signal is of multiple bits which is greater than two, such as four bits, eight bits, sixteen bits, etc. The second second-order harmonic wave 111 and the first second-order harmonic wave 102 are with respective to a second code signal (not shown). Identically, the code of the second code signal is of multiple bits. That is, the codes with respective to the first second-order harmonic waves 101, 102 and the second second-order harmonic wavers 111, 112 are mutually exchanged.

The third second-order harmonic wave 121 and the fourth second-order harmonic wave 132 are with respective to a third code signal (not shown). The code of the third code signal is also of multiple bits. The fourth second-order harmonic wave 131 and the third second-order harmonic wave 122 are with respective to a fourth code signal (not shown). The code of the fourth code signal is also of multiple bits. That is, the codes with respective to the third second-order harmonic waves 121, 122 and the fourth second-order harmonic wavers 131, 132 are mutually exchanged.

In addition, the code signal of the first noise interference wave 103 is generated by taking dot product of the first code signal with the second code signal. In addition, the code signal of the second noise interference wave 113 is generated by taking dot product of the second code signal with the first code signal. Because the operation of dot product is commutative, the first noise interference wave 103 and the second noise interference wave 113 have the same phase and code. The code signal of the third noise interference wave 123 is generated by taking dot product of the third code signal with the fourth code signal. In addition, the code signal of the fourth noise interference wave 133 is generated by taking dot product of the fourth code signal with the third code signal. Identically, the third noise interference wave 123 and the fourth noise interference wave 133 have the same phase and code.

In addition, it is noted that the first second-order harmonic waves 101,102, the second second-order harmonic waves 111,112, the third second-order harmonic waves 121,122, and the fourth second-order harmonic waves 131,132 are the waves with correct code. On the other hand, the first noise interference wave 103, the second noise interference wave 113, the third noise interference wave 123, and the fourth noise interference wave 133 are the waves with incorrect code as mentioned in prior art. In addition, the first noise interference wave 103 and the first second-order harmonic wave 102 are partially overlapped, the second noise interference wave 113 and the second second-order harmonic wave 112 are partially overlapped, the third noise interference wave 123 and the third second-order harmonic wave 122 are partially overlapped, and the fourth noise interference wave 133 and the fourth second-order harmonic wave 132 are partially overlapped.

It is noted that in accordance with a preferred embodiment of the present invention, the first code signal and the third code signal compose a first complementary pair, the second code signal and the fourth code signal compose a second complementary pair. The first complementary pair and the second complementary pair are orthogonal with each other. That is, if the first code signal is A1, the second code signal is A2, the third code signal is B1, the fourth code signal is B2, A1 and B1 would be the first complementary pair, A2 and B2 would be the second complementary pair, and the first complementary pair and the second complementary pair are orthogonal with each other.

Regarding the definition of complementary in the preferred embodiment of the present invention, for example, if the first code signal is A1, the third code signal is B1, the two codes would be a complementary pair when the sum of the result of auto-correlation compression of A1 and A1 and the result of auto-correlation compression of B1 and B1 is 6, and so are the second code signal and the fourth code signal, which can be represented by the functions $A1(n) \otimes A1(n) + B1(n) \otimes B1(n) = \delta(n)$ and $A2(n) \otimes A2(n) + B2(n) \otimes B2(n) = \delta(n)$. Auto-correlation compression technology is well known and thus is not repeated here. The definition of orthogonal in the present invention is that the sidelobe signal can be removed by summing the cross-correlation compression results of the codes of the first complementary pair and the second complementary pair. For example, if A1 is the first code signal, A2 is the second code signal, B1 is the third code signal, B2 is the fourth code signal, and the sum of cross-correlation compression result of A1 and A2 and cross-correlation compression result of B1 and B2 is 0, which can be represented by the function $A1(n) \otimes A2(n) + B1(n) \otimes B2(n) = 0$, then the two complementary pairs are orthogonal with each other. Cross-correlation compression technology is well known and thus is not repeated here.

In addition, the central frequencies of the first second-order harmonic wave 101, the second second-order harmonic wave 111, the third second-order harmonic wave 121, and the fourth second-order harmonic wave 131 are all $f_2-f_1$, the central frequencies of the first second-order harmonic wave 102, the second second-order harmonic wave 112, the third second-order harmonic wave 122, and the fourth second-order harmonic wave 132 are all $2f_1$, the central frequencies of the first noise interference wave 103, the second noise interference wave 113, the third noise interference wave 123, and the fourth noise interference wave 133 are all $f_2+f_1$. The central frequencies of all the waves mentioned in the following step can be referred to here.

After the completion of step S101, the step S102 is carried out to make the second Golay code signal wave be subtracted from the first Golay code signal to generate a fifth Golay code signal wave and make the fourth Golay code signal wave be subtracted from the third Golay code signal wave to generate a sixth Golay code signal wave. In detail, because the first noise interference wave 103 and the second noise interference wave 113 have identical phase and code, the third noise interference wave 123 and the fourth noise interference wave 133 have identical phase and code, the noise interference with incorrect code has been removed after step S101. In the present step S102, as shown in FIG. 2, a subtractor (not shown in the figure) is used to make the second Golay code signal wave 11 be subtracted from the first Golay code signal wave 10 to eliminate the first noise interference wave 103 and the second noise interference wave 113 so as to generate the fifth Golay code signal wave 14. The fifth Golay code signal wave 14 includes two fifth second-order harmonic waves 141,142, wherein the fifth second-order harmonic wave 141 is generated by subtracting the second second-order harmonic wave 111 from the first second-order harmonic wave 101, and the fifth second-order harmonic wave 142 is generated by subtracting the second second-order harmonic wave 112 from the first second-order harmonic wave 102.

In addition, the present step also use a subtractor (not shown) to make the fourth Golay code signal wave 13 be subtracted from the third Golay code signal wave 12 to eliminate the third noise interference wave 123 and the fourth noise interference wave 133 so as to generate the sixth Golay code signal wave 15. The sixth Golay code signal wave 15 includes two sixth second-order harmonic waves 151,152, wherein the sixth second-order harmonic wave 151 is generated by subtracting the fourth second-order harmonic wave 131 from the third second-order harmonic wave 121, and the sixth second-order harmonic wave 152 is generated by subtracting the fourth second-order harmonic wave 132 from the third second-order harmonic wave 122.

After the completion of step S102, step S103 is carried out to perform a first and a second compression filtering process to the fifth Golay code signal wave to generate a first and a second compressed code signal wave and simultaneously process a third and a fourth compression filtering process to the sixth Golay code signal wave to generate a third and a fourth compressed code signal wave. Specifically, as shown in FIG. 3, the first compression filtering process 100 and the second compression filtering process 200 are carried out on the fifth Golay code signal wave 14 simultaneously. As a preferred embodiment, the first compression filtering process 100 is to process cross-correlation compression on the fifth Golay code signal wave 14 and the first code signal by using a filter, and the second compression filtering process 200 is to process cross-correlation compression on the fifth Golay code signal wave 14 and the second code signal by using a filter.

In addition, the present step also processes a third compression filtering process 300 and a fourth compression filtering process 400 on the sixth Golay code signal wave 15 simultaneously. As a preferred embodiment, the third compression filtering process 300 is to process cross-correlation compression on the sixth Golay code signal wave 15 and the third code signal by using a filter, and the fourth compression filtering process 400 is to process cross-correlation compression on the sixth Golay code signal wave 15 and the fourth code signal by using a filter.

After the completion of processing the first compression filtering process 100 on the fifth Golay code signal wave 14, a first compressed code signal wave 16 is generated, which includes two second-order harmonic waves 161,162. Similarly, after the completion of processing the second compression filtering process 200 on the fifth Golay code signal wave 14, a second compressed code signal wave 17 is generated, which also includes two second-order harmonic waves 171, 172.

After the completion of processing the third compression filtering process 300 on the sixth Golay code signal wave 15, a third compressed code signal wave 18 is generated, which includes two second-order harmonic waves 181,182. Similarly, after the completion of processing the fourth compression filtering process 400 on the sixth Golay code signal wave 15, a fourth compressed code signal wave 19 is generated, which also includes two second-order harmonic waves 191, 192. However, because the first compressed code signal wave 16, the second compressed code signal wave 17, the third compressed code signal wave 18, and the fourth compressed code signal wave 19 generated from the step S103 are not fully decoded, step S104 is needed to complete the compression process.

After the completion of step S103, step S104 is carried out to take a sum of the first compressed code signal wave and the third compressed code signal wave to generate a fifth compressed code signal wave and to take a sum of the second compressed code signal wave and the fourth compressed code signal wave to generate a sixth compressed code signal wave. Specifically, as shown in FIG. 4, the present step uses an adder (not shown) to take the sum of the first compressed code signal wave 16 and the third compressed code signal 18 so as to generate the fifth compressed code signal 20, which includes first compressed second-order harmonic waves 201, 202. As a preferred embodiment of the present invention, the code of the first compressed second-order harmonic wave 201 is defined as [6], and the code of the first compressed second-order harmonic wave 202 is defined as [−6].

Moreover, the present step also uses an adder to take the sum of the second compressed code signal wave 17 and the fourth compressed code signal 19 so as to further remove the unnecessary noise (not shown) to generate the sixth compressed code signal 21. The sixth compressed code signal 21 includes second compressed second-order harmonic waves 211, 222. As a preferred embodiment of the present invention, the code of the second compressed second-order harmonic wave 211 is defined as [−δ], and the code of the second compressed second-order harmonic wave 212 is defined as [δ].

After the completion of step S104, step S105 is performed to take the difference between the fifth compressed code signal wave and the sixth compressed code signal wave to generate an image wave which includes at least two imaging second-order harmonic waves. Specifically, the present step uses a subtractor to take the difference between the fifth compressed code signal wave 20 and the sixth compressed code signal wave 21 to generate an image wave 22 which includes two imaging second-order harmonic waves 221, 222. The image wave may include more than two imaging second-order harmonic waves in other embodiments. The imaging second-order harmonic wave 221 is generated by taking the difference between the first compressed second-order harmonic wave 201 and the second compressed second-order harmonic wave 211, and the code of the code signal thereof is [2δ], and the imaging second-order harmonic wave 222 is generated by taking the difference between the first compressed second-order harmonic wave 202 and the second compressed second-order harmonic wave 212, and the code of the code signal thereof is [−2δ].

After the completion of step S105, step S106 is carried out to process ultrasound nonlinear imaging by using the at least two imaging second-order harmonic waves to generate an ultrasound image. In the present step, the imaging second-order harmonic waves 221 and 222 are used for processing ultrasound nonlinear imaging (ultrasound imaging is well known and thus is not repeated here). By using the above mentioned steps provided in accordance with a preferred embodiment of the present invention, image resolution along the axial direction would not be degraded such that a clearer ultrasound image can be generated.

In addition, the technology disclosed in the present invention can be applied to nonlinear imaging or the conditions that the fundamental signal being interfered by the second-order harmonic waves or the second-order harmonic wave being interfered by the fourth-order harmonic wave. Thus, the application of the present invention should not be restricted in nonlinear imaging.

The method of ultrasound nonlinear imaging with high-bit Golay code excitation in accordance with the present invention removes the interference signals prior to the compression process such that the high-bit Golay code can be correctly decoded. Thus, by using the Golay code waveform provided in the present invention, not only the SNR can be enhanced but also eliminate the interference of incorrect code so as to enhance imaging quality.

The detail description of the aforementioned preferred embodiments is for clarifying the feature and the spirit of the present invention. The present invention should not be limited by any of the exemplary embodiments described herein, but should be defined only in accordance with the following claims and their equivalents. Specifically, those skilled in the art should appreciate that they can readily use the disclosed conception and specific embodiments as a basis for designing or modifying other structures for carrying out the same purposes of the present invention without departing from the scope of the invention as defined by the appended claims.

What is claimed is:

1. A method of ultrasound nonlinear imaging with high-bit Golay code excitation comprising the steps of:
   (a) receiving a first Golay code signal wave, a second Golay code signal wave, a third Golay signal wave, and a fourth Golay signal wave, wherein the first Golay code signal wave includes at least two first second-order harmonic waves and at least one first noise interference wave, the second Golay code signal wave includes at least two second second-order harmonic waves and at least one second noise interference wave, the third Golay code signal wave includes at least two third second-order harmonic waves and at least one third noise interference wave, the fourth Golay code signal wave includes at least two fourth second-order harmonic waves and at least one fourth noise interference wave, the above mentioned at least two first second-order harmonic waves are respective to a first code signal and a second code signal, the above mentioned at least two second second-order harmonic waves are respective to the exchanged second code signal and the first code signal, the above mentioned at least two third second-order harmonic waves are respective to a third code signal and a fourth code signal, the above mentioned at least two fourth second-order harmonic waves are respective to the exchanged fourth code signal and the third code signal, the first code signal and the third code signal compose a first complementary pair, the second code signal and the fourth code signal compose a second complementary pair, and the first complementary pair and the second complementary pair are orthogonal by each other;

(b) making the second Golay code signal wave be subtracted from the first Golay code signal wave to eliminate the first noise interference wave and the second noise interference wave to generate a fifth Golay code signal wave, and making the fourth Golay code signal wave be subtracted from the third Golay code signal wave to eliminate the third noise interference wave and the fourth noise interference wave to generate a sixth Golay code signal wave;

(c) performing a first compression filtering process and a second compression filtering process to the fifth Golay code signal wave respectively to generate a first compressed code signal wave and a second compressed code signal wave, and performing a third compression filtering process and a fourth compression filtering process to the sixth Golay code signal wave respectively to generate a third compressed code signal wave and a fourth compressed code signal wave;

(d) taking a sum of the first compressed code signal wave and the third compressed code signal wave to generate a fifth compressed code signal wave, which includes at least two first compressed second-order harmonic waves, and taking a sum of the second compressed code signal wave and the fourth compressed code signal wave to generate a sixth compressed code signal wave, which includes at least two second compressed second-order harmonic waves;

(e) taking the difference between the fifth compressed code signal wave and the sixth compressed code signal wave to generate an image wave which includes at least two imaging second-order harmonic waves; and (f) processing ultrasound nonlinear imaging by using the at least two imaging second-order harmonic waves to generate an ultrasound image;

wherein, the first code signal, the second code signal, the third code signal, and the fourth code signal are high-bit code signals with more than four bits.

2. The method of ultrasound nonlinear imaging with high-bit Golay code excitation of claim 1, wherein code signal of the first noise interference wave is generated by taking dot product of the first code signal with the second code signal, code signal of the second noise interference wave is generated by taking dot product of the second code signal with the first code signal, code signal of the third noise interference wave is generated by taking dot product of the third code signal with the fourth code signal, code signal of the fourth noise interference wave is generated by taking dot product of the fourth code signal with the third code signal.

3. The method of ultrasound nonlinear imaging with high-bit Golay code excitation of claim 1, wherein in the step (b), the fifth Golay code signal includes at least two fifth second-order harmonic waves, and the at least two fifth second-order harmonic waves are generated by subtracting the at least two second second-order harmonic waves from the at least two first second-order harmonic waves.

4. The method of ultrasound nonlinear imaging with high-bit Golay code excitation of claim 1, wherein in the step (b), the sixth Golay code signal includes at least two sixth second-order harmonic waves, and the at least two sixth second-order harmonic waves are generated by subtracting the at least two fourth second-order harmonic waves from the at least two third second-order harmonic waves.

5. The method of ultrasound nonlinear imaging with high-bit Golay code excitation of claim 1, wherein in the step (c), the first compression filtering process is performed by cross-correlation of the fifth Golay code signal wave and the first code signal, the second compression filtering process is performed by cross-correlation of the fifth Golay code signal wave and the second code signal, the third compression filtering process is performed by cross-correlation of the sixth Golay code signal wave and the third code signal, and the fourth compression filtering process is performed by cross-correlation of the sixth Golay code signal wave and the fourth code signal.

* * * * *